(12) United States Patent
Tankovich et al.

(10) Patent No.: US 6,613,042 B1
(45) Date of Patent: Sep. 2, 2003

(54) RAINBOW LASER

(76) Inventors: Nikolai Tankovich, 9361 Stargaze Ave., San Diego, CA (US) 92129; Alexie Lukashev, 3574 Caminito El Rincon #97, San Diego, CA (US) 92130

( * ) Notice: Subject to any disclaimer, the term of this patent is extended or adjusted under 35 U.S.C. 154(b) by 0 days.

(21) Appl. No.: 09/608,020

(22) Filed: Jun. 30, 2000

(51) Int. Cl.[7] ............................................... A61B 18/20
(52) U.S. Cl. ................................ 606/10; 606/3; 606/13
(58) Field of Search ........................ 372/1–42; 606/1–21

(56) References Cited

U.S. PATENT DOCUMENTS

| | | | | |
|---|---|---|---|---|
| 3,693,623 A | * | 9/1972 | Harte et al. ................... 606/9 |
| 4,386,428 A | * | 5/1983 | Bauer ........................... 372/41 |
| 4,399,539 A | * | 8/1983 | White ............................ 372/3 |
| 5,134,622 A | * | 7/1992 | Deacon ......................... 372/21 |
| 5,144,630 A | * | 9/1992 | Lin ............................. 359/330 |
| 5,620,478 A | * | 4/1997 | Eckhouse ...................... 607/88 |
| 5,640,405 A | * | 6/1997 | Wallace et al. ................ 372/21 |
| 5,658,323 A | * | 8/1997 | Miller .......................... 607/89 |
| 5,707,403 A | * | 1/1998 | Grove et al. ................... 607/89 |
| 5,735,844 A | * | 4/1998 | Anderson et al. .............. 606/9 |
| 5,737,347 A | * | 4/1998 | Scheps et al. ................. 372/23 |
| 5,885,273 A | * | 3/1999 | Eckhouse et al. .............. 606/9 |
| 5,995,867 A | * | 11/1999 | Zavislan et al. ............. 600/476 |
| 6,165,171 A | * | 12/2000 | Tobinick ...................... 606/11 |
| 6,273,885 B1 | * | 8/2001 | Koop et al. .................... 606/9 |

* cited by examiner

*Primary Examiner*—Roy D. Gibson
*Assistant Examiner*—Henry M. Johnson
(74) *Attorney, Agent, or Firm*—John R. Ross; John R. Ross, III

(57) ABSTRACT

A single laser system that operates at any one or any combination of at least five wavelengths each of which are important to medical facilities offering laser cosmetic services. The present invention includes appropriate laser optics and a crystal rod configured to produce a first pulsed laser beam, and appropriate laser optics and a second crystal rod configured to produce a second pulsed laser beam. Both rods are pumped simultaneously preferably from the same pump source. Beams from each of these lasers are frequency doubled using frequency-doubling crystals to produce third and fourth laser beams. The frequencies of the first and second beams are also combined in a sum frequency generating crystal to produce a fifth laser beam. In a preferred embodiment the first and second laser beams are produced using YAP:Nd crystals with wavelengths of 1079 nm and 1341 nm. The third and fourth laser beams at 539.5 nm and 670.5 nm are produced using KTP frequency doubling crystals and the fifth laser beam at about 598 nm is produced using a KTA sum frequency crystal. Thus, five different beams are produced with this laser system. All or any combination of these five beams are preferably combined by coupling them into a single optical fiber so that the beam can be easily transmitted to the place of treatment.

17 Claims, 2 Drawing Sheets

RAINBOW LASER

This invention relates to laser systems and in particular to multi-wavelength laser systems.

BACKGROUND OF THE INVENTION

Use of lasers for medical purposes is well established. Lasers are used extensively for cosmetic purposes such as hair removal, vein treatment, skin rejuvenation, treatment of telangeatesia and treatment of port wine stain. Each of these treatments is preferably performed with a laser producing laser pulses at a wavelength chosen to be most effective for the particular treatment. For example, a Nd:YAG laser operating at 1064 nm may be used for hair removal and certain types of vein treatment. A Nd:YAG laser operating at 1320 nm may be used for skin rejuvenation and micro skin surgery. Treatment of port wine stains is usually performed using a dye laser operating at a wavelength of 577 nm. Lasers used for treatment of small surface veins do not work very well for treatment of larger deeper veins. As a consequence a medical facility offering a variety of laser-based cosmetic services in the past has been required to acquire and maintain several separate laser systems. This is expensive.

Some wavelengths are very preferentially absorbed in a particular type of tissue such as when the tissue contains a particular chromophore that has a peak or reletively high absorption at the particular wavelength. Use of a laser beam matched to a peak or relatively high absorption in tissue to treat the tissue is referred to as "selective thermolysis". Some wavelengths are absorbed relatively uniformly in tissue and when these wavelengths are used to treat the tissue it is referred to as "non-selective thermolysis".

What is needed is a single laser that can produce simultaneously laser light at a variety of wavelengths needed in medical facilities specializing is cosmetic care.

SUMMARY OF THE INVENTION

The present invention provides a single laser system that operates at any one or any combination of at least five wavelengths each of which are important to medical facilities offering laser cosmetic services. It includes appropriate laser optics and a crystal rod configured to produce a first pulsed laser beam, and appropriate laser optics and a second crystal rod configured to produce a second pulsed laser beam. Both rods are pumped simultaneously preferably from the same pump source. Beams from each of these lasers are frequency doubled using frequency-doubling crystals to produce third and fourth laser beams. The frequencies of the first and second beams are also combined in a sum frequency generating crystal to produce a fifth laser beam. In a preferred embodiment the first and second laser beams are produced using YAP:Nd crystals with wavelengths of 1079 nm and 1341 nm. The third and fourth laser beams at 539.5 nm and 670.5 nm are produced using KTP frequency doubling crystals and the fifth laser beam at about 598 nm is produced using a KTA sum frequency crystal. Thus, five different beams are produced with this laser system. All or any combination of these five beams are preferably combined by coupling them into a single optical fiber so that the beam can be easily transmitted to the place of treatment.

DETAILED DESCRIPTION OF PREFERRED EMBODIMENTS

Preferred embodiments of the present invention may be described by reference to the drawings.

First Preferred Embodiment

Figure 1:
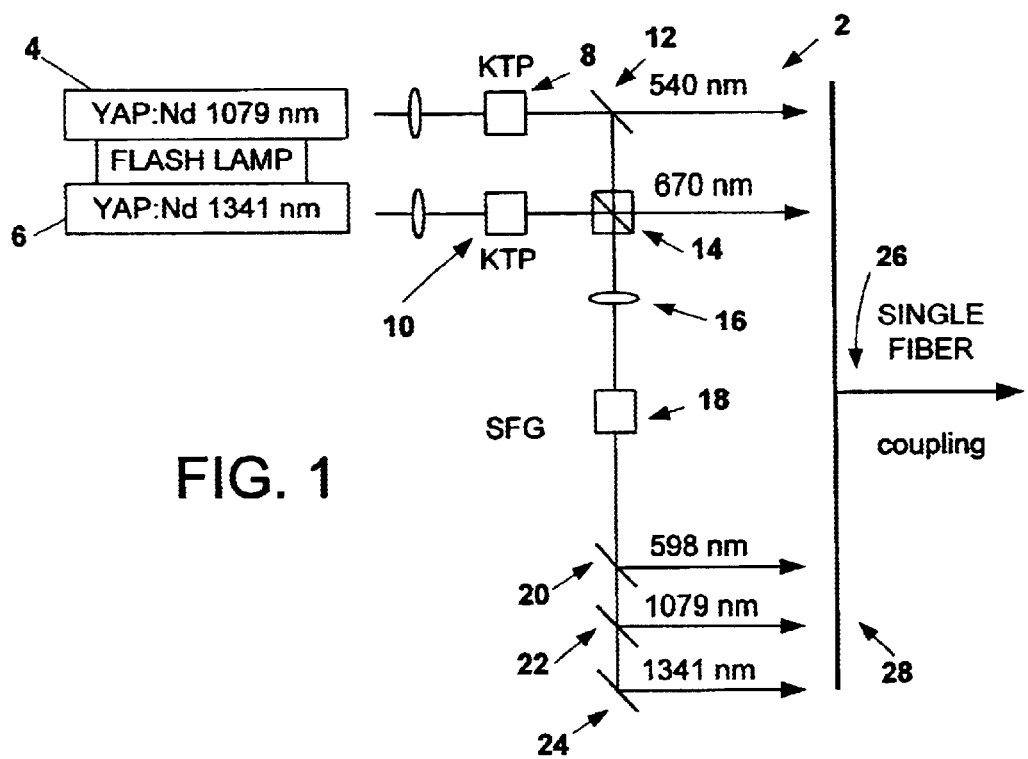
FIG. 1 is a drawing showing the principal features of a preferred embodiment of the present invention.
Figure 2:
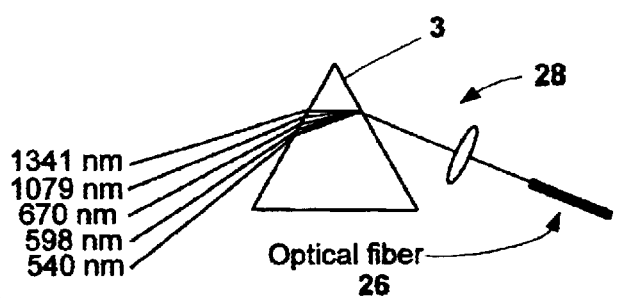
FIG. 2 is a drawing explaining a technique for coupling five separate wavelengths into a single optical fiber.

A first preferred embodiment of the present invention is shown in FIGS. 1 and 2. This is a five-beam laser system 2. A pulsed laser beam is produced with a YAP:Nd crystal rod 4 that is coated at its ends with special reflective coatings, using well-known techniques, chosen to produce 1079-nm light. A second beam is produced with a second YAP:Nd crystal rod 6 which is also coated with special reflective coatings chosen to produce 1341-nm light. For these lasers the crystal orientation determines the polarization of the output beams. In this preferred embodiment the crystals are arranged so that the 1079-nm beam is horizontally polarized and the 1341 nm beam is vertically polarized. Both rods are preferably pumped from a common pump source or separate sources driven by a common power supply. The optical components needed for these well-known laser configurations are chosen to produce 18 J pulses for the 1341 nm beam and about 22 J pulses for the 1079 nm beam. Pulse durations are from about 10 to 20 milliseconds. The configurations should preferably be designed for operator selected pulse rates between 0.5 Hz and 100 Hz. In typical operation the laser is operated in bursts of pulses with each burst containing several pulses (such as 3 to 15 pulses) at selected pulse repetition rates. Preferably the controls are configured so that the operator can select a burst repetition rate up to about 2 Hz. Thus the operator could select a pulse repetition rate of 100 Hz with 5 pulses per burst and a burst repetition rate of 2 Hz. This would provide 10 pulses per second.

Both beams are frequency doubled using frequency-doubling crystals 8 and 10 to produce light at 539.5 nm and 670.5 nm. The 539.5 nm light is separated from the 1079 nm light with mirror 12 coated with a coating chosen to transmit 539.5 nm and reflect 1079 nm light. Therefore, the 539.5 nm light passes horizontally as shown in FIG. 1 and the 1079 nm light reflects downward as shown on the drawing.

Optic 14 is a dichroic mirror that is coated to transmit 670.5 nm and 1079 nm light and to reflect 1341 nm light. The 670.5 nm light is transmitted in the horizontal direction and the 1079 nm light is transmitted downward and the 1341 nm light is reflected downward.

The combined beam of the 1079 nm light and the 1341 nm light is focused by optic 16 into sum frequency generation crystal 18 which converts a portion of the combined beam into light at 598 nm so that the light exiting the crystal is a combined beam having light at wavelengths of 598 nm, 1079 nm and 1341 nm. These wavelengths are then preferably separated using mirror 20 which is coated to reflect 598 nm light and transmit light at 1079 nm and 1341 nm, mirror 22 which is coated to reflect light at 1079 nm and transmit light at 1341 nm and mirror 24 which reflects 1341 nm light.

Figure 3:
FIG. 3 is a drawing of a laser surgery hand piece.
Figure 4:
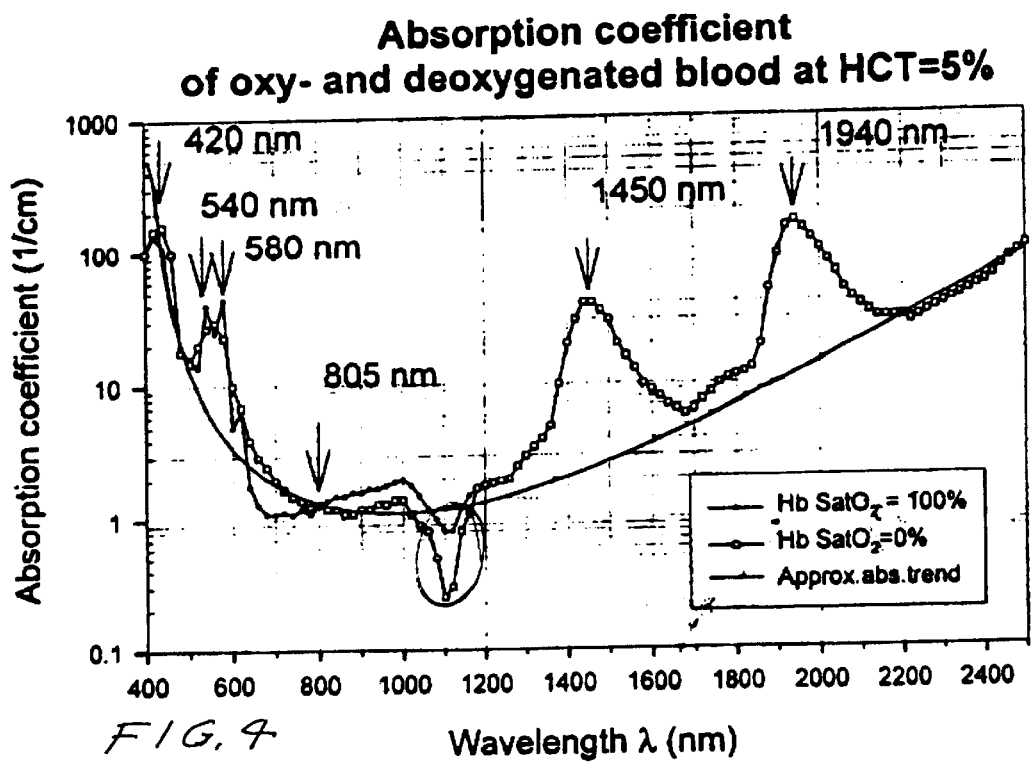
FIG. 4 is a graph of absorption coefficient v wavelength for blood.
Figure 5:
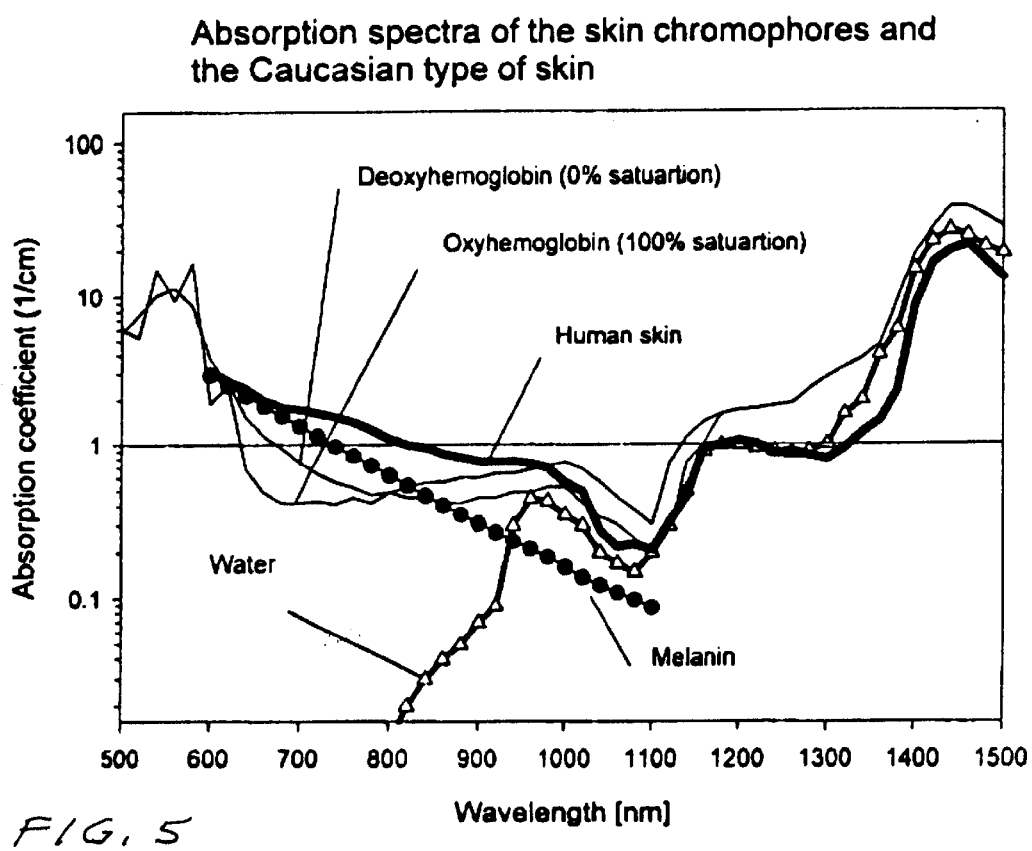
FIG. 5 is a graph of absorption coefficient v wavelength for Caucasian skin.

The five resulting separate beams at the respective wavelengths of 539.5 nm, 670.5 nm, 598 nm, 1079nm and 1341 nm are all coupled into a single optical fiber 26 as shown in FIG. 2 using prism 3. The optical fiber then may provide the combined beam to a collimated zoom hand piece (see FIG. 3) that is used for cosmetic treatment. If fewer than all of the wavelengths are desired for the treatment (which will usually be the case) the not wanted wavelengths can be blocked just upstream of the coupling 28.

Optical Components

The various optical components needed to fabricate the laser system described above are available from normal optics suppliers and techniques for arranging the components are well known to persons skilled in the laser-optics art. For example the YAP:Nd rods for production of the 1079 nm and 1341 nm beams are available from Crytur, Ltd. with offices in Palackeho175, 51101 Tumov, Czeck Republec and Scientific Material Corp. with offices in Bozemon, Mont. Optics for arranging the resonator cavities are available from CVI Corp. with offices in Albuquerque, N. Mex. Flash lamp pumps for these crystal rods are available from Perkin Elmer with offices in Sunnyvale, Calif. KTP crystals suitable for doubling the frequencies of the 1079 nm and the 1341 nm beams are available from Crystal Associates with offices in East Hanover, N.J. and Crystal Technology, Inc. with offices in Palo Alto, Calif. The sum frequency crystal shown at 16 for combining the 1079 nm beam and the 1341 nm beam to produce the 598 nm wavelength preferably is a KTA crystal available from Crystal Associates, Inc. Mirrors 12, 20, 22, and 24 and the optics shown in FIG. 2 are available from CVI Corp.

Preferred Specifications

The power supply and the flash lamp pump source and crystal rod should be sized to pulse energies of 22 J per pulse for the 1079 mn beam and about 18 J per pulse for the 1341 nm beam. Energies per pulse at the other wavelengths are preferably about 4 J at 539.5 nm, 3.5 J at 598 nm and 3 J at 670.5 nm. The beam diameters prior to coupling into the optical fiber optic is about 3 mm or more. The beams are normally focused onto the skin surface to produce fluences in the range of about 30 to 90 J per cm during the treatment period. Fluencies in excess of 50 J per $cm^2$ could cause severe skin damage. However, damage can be avoided or minimized with prior, simultaneous or immediately subsequent cooling.

Treatment Wavelengths

With this one laser system a large variety of laser treatments can be provided. The wavelength 1079 nm is partially absorbed in melanin and only slightly absorbed in oxyhemoglobin and water. Thus, this beam is preferred for hair removal and treatment of larger veins. The wavelength 1341 nm is more highly absorbed in water than the 1079 nm beam so the 1341 nm beam is good for collagen shrinking, skin rejuvenation, small vein treatment and microsurgery. The 670.5 nm beam is highly absorbed in melanin so it is good for hair removal and treatment of pigmented lesions. The 539.5 nm beam is strongly absorbed in oxyhemoglobin and is good for treatment of small vascular lesions and telangeatesia. The 598 nm beam has an absorption peak in oxyhemoglobin so it is preferred for treatment of port wine stain. The combination of the 1079 nm and the 1341 nm beams works well for treatment of hair removal, skin rejuvenation and treatment of larger blood veins. The combination of 670.5 nm and 1079 nm beams is good for hair removal and small vein treatment. Combination of selective 598 nm and non-selective 1079 and/or 1341 nm is for better treatment of large and deep port wine stains and hemangiomas. Combinations covering the entire range of wavelengths available are useful in some cases for treatment of large and small veins at the same time. These include the combinations of 539.5 nm, 1079 nm and 1341 nm and the combination of all of the wavelengths.

Preferred Wavelength Combinations

For many treatments a combination of selective thermolysis and non-selective thermolysis is preferred. The combinations provide a dual benefit.

For example a preferred hair removal method is to heat melanin in hair follicle matrix and hair shaft at 670.5 nm (selective thermolysis) and to heat the surrounding tissue with 1079 nm (non-selective thermolysis). This damages the melanin-rich hair tissue as well as the surrounding tissue providing nutrition to the hair. Preferably the skin surface is cooled before, during and after the treatment.

A combination of 598 nm, 539.5 nm and 670.5 nm with skin surface cooling (before, during and after) is a preferred treatment for port wine stain removal. The combination of 598 nm and 1079 nm with skin cooling is a good combination for capillary and cavemose hermangiomas treatmant, the 598 nm wavelength being directed to blood vessel coagulation in small blood vessles and the 1079 nm wavelength being directed to the larger deeper vessels.

A good treatment for subsurface collagen shrinkage for wrinkle removal, stretch mark and keloid scar treatment is to use 1341 nm combined with deep heating of the reticular dermis with 1079 nm. Skin surface cooling before, during and after is preferred.

Other preferred combinations are microsurgery of skin lesions with 1341 nm (warts, candelomas, skin tags, etc.), and other organ pathologies(such as bronchial tumors, intestine and stomach polyps and tumors, vocal cord calcification, uterine cervix lesion ablation, etc.) with superficial small blood vessel coagulation may be treated with 539.5 nm. Preferably no cooling is provided with these procedures.

The 1079 nm wavelength by itself is a preferred wavelength for small (up to 3 mm) veins and hair removal by uniform tissue coagulation. This 1079 nm wavelength is more effective than 1064 nm because its oxyhemoglobin absorption is 42 percent closer to the minimum oxyhemoglobin spike at 1100 nm as shown in FIGS. 1 and 2. This means that blood in large vessels are heated more uniformly as compared to a wavelength which is strongly absorbed in blood in which case a shield can be created at the edge of the vessel nearest the skin surface.

Although the present invention has been described in terms of preferred embodiments the reader should understand many changes and additions could be made without changing the nature of the invention. For example, potential crystals other than KTP for harmonic generation from 1341 nm to 670.5 nm and from 1079 nm to 539.5 nm include: BBO, KTA, $KNbO_3$, $LiNbO_3$ and RTA. Potential crystals other than KTA for sum frequency generation include BBO, CDA, KTP, $KNbO_3$, $LiNbO_3$ and RTA. The other class of very promising crystals for frequency doubling and sum frequency generations are periodically polled (PP) crystals such $LiNbO_3$ (PPLN), KTP(PPKTP), RTA(PPRTA). Instead of starting with lasers producing 1079 nm and 1341 nm light, other combinations of laser beams could be used and these frequency doubled to produce light at wavelengths half as long as the beginning wavelengths and also combined in a sum frequency generator to produce light at a wavelength corresponding to the sum of the frequency of the starting wavelengths. Other possible combinations are: Nd dopped laser crystals such as GGG(Gadolinium Gallium Garnet), GSGG(Gadolinium Scandium Gallium Garnet), YAG (Yttrium Aluminum Garnet), YLF(Yttrium Lithium Fluoride), YVO(Yttrium Orthovanadate) with the first wavelength around 1050–1100 nm and the second wavelength around 1300–1380 nm.

Therefore, the scope of the invention is to be determined by the appended claims and their legal equivalents.

We claim:

1. A laser system that is operable at any of at least five wavelengths comprising:
   A) laser optics and a first YAP:Nd crystal rod having reflective coatings to cause said first crystal rod to produce a first pulsed laser beam at a first wavelength of about 1079 nm,
   B) laser optics and a second crystal rod configured to produce a second laser beam at a second wavelength,
   C) a pumping means for pumping both first and second rods are simultaneously,
   D) a first frequency doubling means to double the first laser beam to produce a third laser beam with a wavelength of one half of said first wavelength,
   E) a second frequency doubling means to double the second laser beam to produce a fourth laser beam with a wavelength of one half of said second wavelength,
   F) a sum frequency generation means for combining wavelengths of said first laser beam and said second laser beam to produce a fifth laser beam with a wavelength corresponding to the sum of the frequency of said first laser beam and the frequency of said second laser beam,
   G) an optical waveguide for transmitting a portion or all of said first, second, third, fourth and fifth laser beam, and
   H) a coupling means for coupling all or a portion of the first, second, third, fourth, and fifth laser beams into a first end of the optical wave guide.

2. A laser system as in claim 1 and further comprising a hand piece connected at a second end of said optical waveguide.

3. A laser system as in claim 1 wherein said first frequency doubling means comprises a KTP crystal.

4. A laser system as in claim 1 wherein said second frequency doubling means comprises a KTP crystal.

5. A laser system that is operable at any of at least five wavelengths comprising:
   A) laser optics and a first crystal rod configured to produce a first pulsed laser beam at a first wavelength,
   B) laser optics and a second crystal comprised of a YAP:Nd crystal rod having a reflective coating to cause said YAP:Nd crystal rod to produce a second laser beam at a second wavelength of about 1341.
   C) a pumping means for pumping both first and second rods are simultaneously,
   D) a first frequency doubling means to double the first laser beam to produce a third laser beam with a wavelength of one half of said first wavelength,
   E) a second frequency doubling means to double the second laser beam to produce a fourth laser beam with a wavelength of one half of said second wavelength,
   F) a sum frequency generation means for combining wavelengths of said first laser beam and said second laser beam to produce a fifth laser beam with a wavelength corresponding to the sum of the frequency of said first laser beam and the frequency of said second laser beam,
   G) an optical waveguide for transmitting a portion or all of said first, second, third, fourth and fifth laser beam, and
   H) a coupling means for coupling all or a portion of the first, second, third, fourth, and fifth laser beams into a first end of the optical wave guide.

6. A laser system that is operable at any of at least five wavelengths comprising:
   A) laser optics and a first YAP:Nd crystal rod having reflective coatings to cause said first crystal rod to produce a first pulsed laser beam at a first wavelength,
   B) laser optics and a second YAP:Nd crystal rod having reflective coatings to cause said second crystal rod to produce a second laser beam at a second wavelength,
   C) a pumping means for pumping both first and second rods are simultaneously,
   D) a first frequency doubling means to double the first laser beam to produce a third laser beam with a wavelength of one half of said first wavelength,
   E) a second frequency doubling means to double the second laser beam to produce a fourth laser beam with a wavelength of one half of said second wavelength,
   F) a sum frequency generation means for combining wavelengths of said first laser beam and said second laser beam to produce a fifth laser beam with a wavelength corresponding to the sum of the frequency of said first laser beam and the frequency of said second laser beam,
   G) an optical waveguide for transmitting a portion or all of said first, second, third, fourth and fifth laser beam, and
   H) a coupling means for coupling all or a portion of the first, second, third, fourth, and fifth laser beams into a first end of the optical wave guide.

7. A laser treatment process using a laser system comprising:
   A) laser optics and a first YAP:Nd crystal rod having reflective coatings to cause said first crystal rod to produce a first pulsed laser beam at a first wavelength at about 1079 nm,
   B) laser optics and a second YAP:ND crystal rod having reflective coatings to cause said second crystal rod to produce a second laser beam at a second wavelength of about 1341 nm,
   C) a pumping means for pumping both first and second rods are simultaneously,
   D) a first frequency doubling means to double the first laser beam to produce a third laser beam with a wavelength of one half of said first wavelength,
   E) a second frequency doubling means to double the second laser beam to produce a fourth laser beam with a wavelength of one half of said second wavelength,
   F) a sum frequency generation means for combining wavelengths of said first laser beam and said second laser beam to produce a fifth laser beam with a wavelength corresponding to the sum of the frequency of said first laser beam and the frequency of said second laser beam,
   G) and optical waveguide for transmitting a portion or all of said first, second, third, fourth and fifth laser beam, and
   H) a coupling means for coupling all or a portion of the first, second, third, fourth, and fifth laser beams into a first end of the optical wave guide;
   said laser system being operable at any of at least five wavelengths, said treatment process comprising the steps of:
   1) operating the laser system,
   2) coupling at least two of said laser beams into said coupling means to produce a combined beam, and
   3) treating tissue with said combined beam.

8. A process as in claim 7 wherein a combination of wavelengths at about 1079 nm and about 670.5 nm with surface skin cooling is used for hair removal.

9. A process as in claim 8 wherein skin surface cooling is provided before, during and after laser beam use.

10. A process as in claim 7 wherein a combination of wavelengths at about 598 nm, about 539.5 nm and about 670.5 nm with surface skin cooling is used for portwine stain removal.

11. A process as in claim 7 wherein a combination of wavelengths at about 598 nm and about 1079 nm with surface skin cooling is used for blood vessel coagulation of large and small vessels.

12. A process as in claim 7 wherein a combination of wavelengths at about 1079 nm and about 1341 nm with surface skin cooling is used for subsurface collagen shrinking.

13. A process as in claim 7 wherein said plurality of medical treatments include use of 1079 nm wavelength for hair removal.

14. A process as in claim 7 wherein said tissue treatment include use of 1079 nm wavelength for destruction of small blood vessels having thickness of up to 3 mm.

15. A process as in claim 14 wherein skin surface cooling is provided before, during and after laser beam use.

16. A process as in claim 7 wherein said tissue treatment comprises microsurgery.

17. A process as in claim 8 wherein skin surface cooling is provided before, during and after laser beam use.

* * * * *